United States Patent
Plumptre et al.

(10) Patent No.: US 9,616,179 B2
(45) Date of Patent: *Apr. 11, 2017

(54) RESETTING MECHANISM FOR A DRUG DELIVERY DEVICE

(75) Inventors: David Plumptre, Droitwich Spa (GB); Christopher Jones, Tewkesbury (GB)

(73) Assignee: SANOFI—AVENTIS DEUTSCHLAND GMBH, Frankfurt am Main (DE)

( * ) Notice: Subject to any disclaimer, the term of this patent is extended or adjusted under 35 U.S.C. 154(b) by 218 days.

This patent is subject to a terminal disclaimer.

(21) Appl. No.: 13/375,183

(22) PCT Filed: May 28, 2010

(86) PCT No.: PCT/EP2010/057483
§ 371 (c)(1),
(2), (4) Date: Mar. 12, 2012

(87) PCT Pub. No.: WO2010/139637
PCT Pub. Date: Dec. 9, 2010

(65) Prior Publication Data
US 2012/0172814 A1  Jul. 5, 2012

Related U.S. Application Data

(60) Provisional application No. 61/182,820, filed on Jun. 1, 2009.

(30) Foreign Application Priority Data

Jul. 10, 2009 (EP) ..................... 09009057

(51) Int. Cl.
*A61M 5/315* (2006.01)
*A61M 5/24* (2006.01)

(52) U.S. Cl.
CPC .... *A61M 5/31543* (2013.01); *A61M 5/31551* (2013.01); *A61M 5/31585* (2013.01);
(Continued)

(58) Field of Classification Search
CPC .. A61M 2005/2407; A61M 2005/2488; A61M 2005/3125; A61M 5/31543;
(Continued)

(56) References Cited

U.S. PATENT DOCUMENTS 2,816,543 A * 12/1957 Scherer ................... A61M 5/30
604/68
3,768,135 A * 10/1973 Maguire ................ B26B 21/26
29/820

(Continued)

FOREIGN PATENT DOCUMENTS

WO 96/32973 10/1996
WO 2004/078241 9/2004
(Continued)

OTHER PUBLICATIONS

International Search Report and Written Opinion for International App. No. PCT/EP2010/057483, completed Aug. 4, 2010.
(Continued)

*Primary Examiner* — Bhisma Mehta
*Assistant Examiner* — Matthew A Engel
(74) *Attorney, Agent, or Firm* — McDonnell Boehnen Hulbert & Berghoff LLP

(57) ABSTRACT

A driver for driving a spindle of a drug delivery device is provided. Said driver comprises a first component and a second component rotationally coupled to said first component. During resetting of said drug delivery device, said first component is rotationally decoupled from said second component.

15 Claims, 10 Drawing Sheets

(52) U.S. Cl.
CPC ..... *A61M 5/31511* (2013.01); *A61M 5/31541* (2013.01); *A61M 5/31558* (2013.01); *A61M 5/31575* (2013.01); *A61M 2005/2407* (2013.01); *A61M 2005/2488* (2013.01); *A61M 2005/2492* (2013.01); *A61M 2005/3152* (2013.01)

(58) Field of Classification Search
CPC .......... A61M 5/31551; A61M 5/31585; A61M 5/31541; A61M 5/31575; A61M 5/31558
USPC .................. 604/110, 218, 136, 197, 68, 207
See application file for complete search history.

(56) References Cited

U.S. PATENT DOCUMENTS

| | | | | |
|---|---|---|---|---|
| 3,882,863 | A * | 5/1975 | Sarnoff et al. ................ | 604/136 |
| 4,596,556 | A * | 6/1986 | Morrow et al. ................ | 604/70 |
| 5,304,152 | A * | 4/1994 | Sams ............... | A61M 5/31553 |
| | | | | 604/207 |
| 5,383,851 | A * | 1/1995 | McKinnon et al. ............ | 604/68 |
| 5,423,752 | A * | 6/1995 | Haber ..................... | A61M 5/19 |
| | | | | 222/137 |
| 5,503,627 | A * | 4/1996 | McKinnon et al. ............ | 604/72 |
| 5,865,795 | A * | 2/1999 | Schiff et al. ..................... | 604/70 |
| 5,891,086 | A * | 4/1999 | Weston ............................ | 604/70 |
| 6,235,004 | B1 * | 5/2001 | Steenfeldt-Jensen ...................... | |
| | | | | A61M 5/31551 |
| | | | | 604/207 |
| 7,195,616 | B2 * | 3/2007 | Diller et al. .................. | 604/224 |
| 7,241,278 | B2 * | 7/2007 | Moller .................... | A61M 5/24 |
| | | | | 604/211 |
| 7,678,084 | B2 * | 3/2010 | Judson et al. ................ | 604/187 |
| 7,699,802 | B2 * | 4/2010 | Steinway et al. ............... | 604/68 |
| 8,070,727 | B2 | 12/2011 | Veasey et al. | |
| 8,075,517 | B2 * | 12/2011 | Karlsson et al. ................. | 604/82 |
| 8,672,896 | B2 * | 3/2014 | Plumptre .......... | A61M 5/31541 |
| | | | | 604/207 |
| 2004/0210199 | A1 | 10/2004 | Atterbury et al. | |
| 2004/0236285 | A1 * | 11/2004 | Fisher ................. | A61M 5/3158 |
| | | | | 604/207 |
| 2006/0089593 | A1 * | 4/2006 | Landau et al. .................. | 604/68 |
| 2006/0089594 | A1 * | 4/2006 | Landau ............ | 604/68 |
| 2006/0153693 | A1 | 7/2006 | Fiechter et al. | |
| 2006/0173408 | A1 * | 8/2006 | Wyrick ............... | A61M 5/2033 |
| | | | | 604/110 |
| 2006/0229570 | A1 * | 10/2006 | Lovell ..................... | A61M 5/20 |
| | | | | 604/218 |
| 2006/0270985 | A1 * | 11/2006 | Hommann et al. ........... | 604/136 |
| 2007/0093761 | A1 * | 4/2007 | Veasey ............. | A61M 5/31546 |
| | | | | 604/207 |
| 2009/0275914 | A1 * | 11/2009 | Harms .................... | A61M 5/24 |
| | | | | 604/506 |
| 2010/0324495 | A1 * | 12/2010 | Jones ...................... | A61M 5/24 |
| | | | | 604/207 |
| 2010/0324527 | A1 * | 12/2010 | Plumptre .......... | A61M 5/31536 |
| | | | | 604/500 |
| 2010/0324528 | A1 * | 12/2010 | Plumptre ................ | A61M 5/24 |
| | | | | 604/506 |
| 2010/0331792 | A1 * | 12/2010 | Plumptre .......... | A61M 5/31525 |
| | | | | 604/207 |
| 2012/0172814 | A1 * | 7/2012 | Plumptre .......... | A61M 5/31543 |
| | | | | 604/207 |

FOREIGN PATENT DOCUMENTS

| | | |
|---|---|---|
| WO | 2006/114395 | 11/2006 |
| WO | 2008/031235 | 3/2008 |
| WO | 2008/116766 | 10/2008 |

OTHER PUBLICATIONS

European Search Report for European App. No. 09009057, completed Jun. 10, 2010.
International Preliminary Report on Patentability for International App. No. PCT/EP2010/057483, issued Dec. 6, 2011.

* cited by examiner

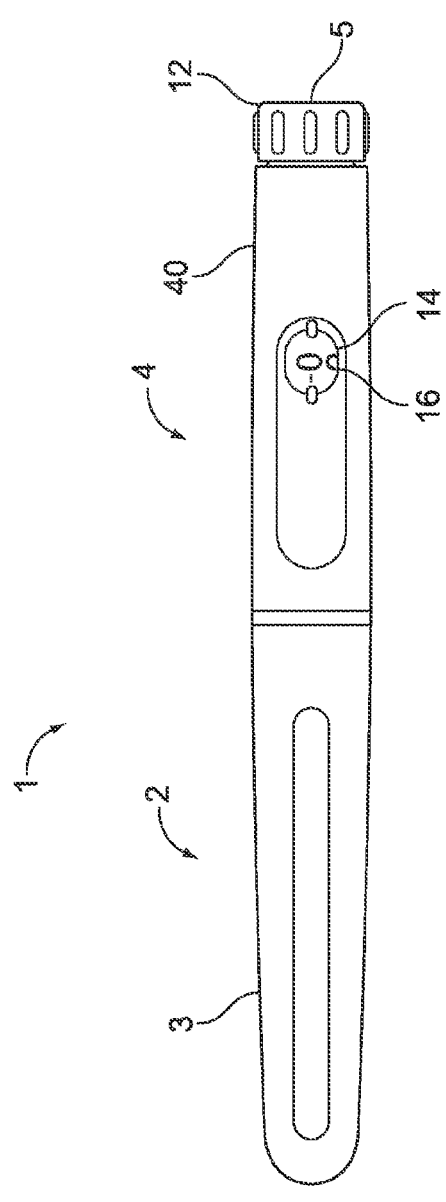
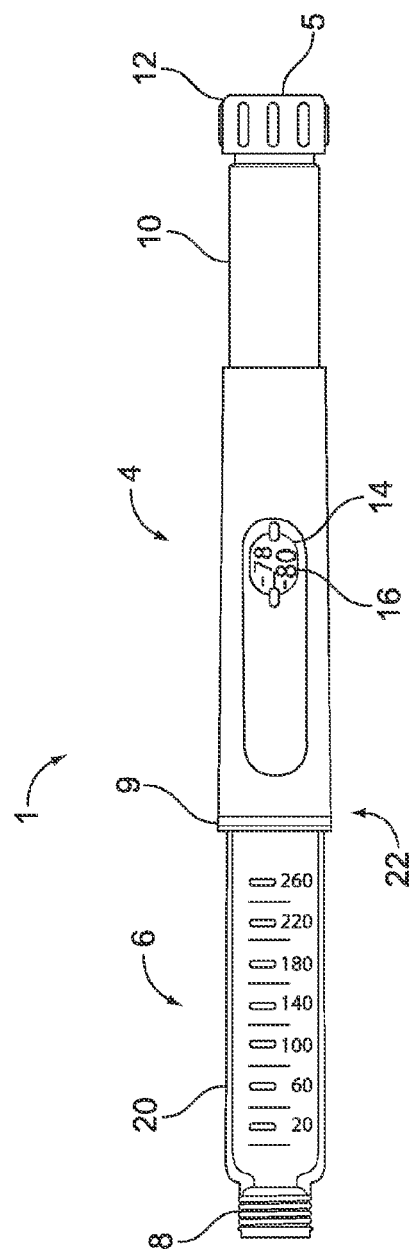
FIG. 1
FIG. 2

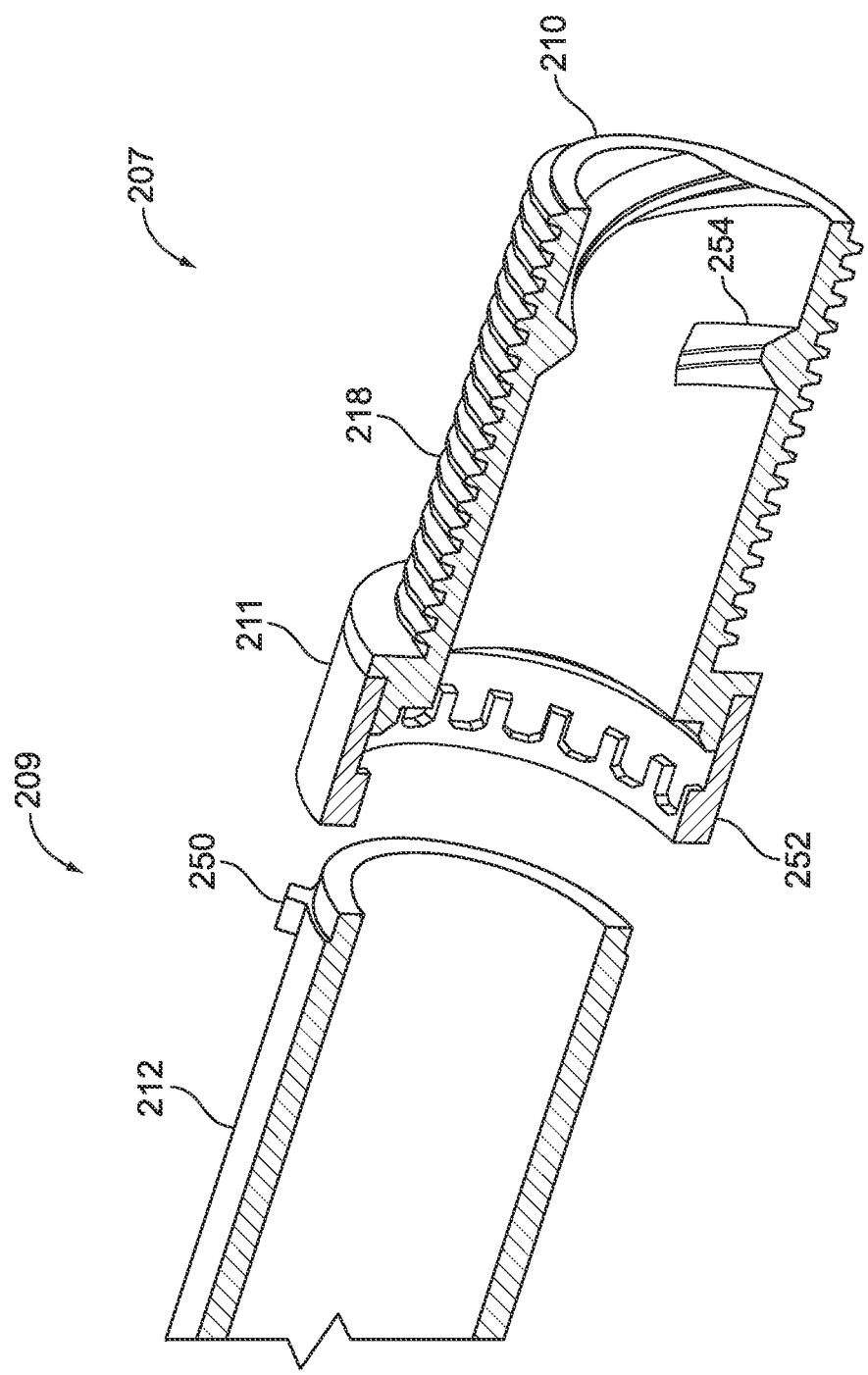

RESETTING MECHANISM FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2010/057483 filed May 28, 2010, which claims priority to U.S. Provisional Patent Application No. 61/182,820 filed on Jun. 1, 2009 and to European Patent Application No. 09009057.2 filed on Jul. 10, 2009. The entire disclosure contents of these applications are herewith incorporated by reference into the present application.

FIELD OF INVENTION

The present application is generally directed to dose setting mechanisms for drug delivery devices. More particularly, the present application is generally directed to resettable dose setting mechanisms for drug delivery devices.

Pen type drug delivery devices provide for self administration of medicinal product from a multi-dose cartridge. A resettable pen type drug delivery device allows a user to replace an empty multi-dose cartridge with a new cartridge. Consequently, the user is called upon to re-set a dose setting mechanism of the drug delivery device. Aspects of the invention may be equally applicable in other scenarios as well.

BACKGROUND

Pen type drug delivery devices have application where regular injection by persons without formal medical training occurs. This may be increasingly common among patients having diabetes where self-treatment enables such patients to conduct effective management of their disease.

There are basically two types of pen type delivery devices: resettable devices (i.e., reusable) and non-resettable (i.e., disposable). These types of pen delivery devices (so named because they often resemble an enlarged fountain pen) are generally comprised of three primary elements: (i) a cartridge section that includes a cartridge often contained within a housing or holder; (ii) a needle assembly connected to one end of the cartridge section; and (iii) a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then a dose is administered. Such removable needle assemblies may be threaded onto, or pushed (i.e., snapped) onto the pierceable seal end of the cartridge assembly.

The dosing section or dose setting mechanism is typically the portion of the pen device that is used to set a dose. During an injection, a spindle contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

Different types of pen delivery devices, including disposable (i.e., non-resettable) and reusable (i.e., resettable) varieties, have evolved over the years. For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

In contrast to typical disposable pen type devices, typical reusable pen delivery devices feature essentially two main reusable components: a cartridge holder and a dose setting mechanism. After a cartridge is inserted into the cartridge holder, this cartridge holder is attached to the dose setting mechanism. The user uses the dose setting mechanism to select a dose. Before the user injects the set dose, a replaceable double-ended needle assembly is attached to the cartridge housing.

This needle assembly may be threaded onto or pushed onto (i.e., snapped onto) a distal end of the cartridge housing. In this manner, a double ended needle mounted on the needle assembly penetrated through a pierceable seal at a distal end of the cartridge. After an injection, the needle assembly is removed and discarded. After the insulin in the cartridge has been exhausted, the user detaches the cartridge housing from the dose setting mechanism. The user can then remove the empty cartridge from the cartridge retainer and replace the empty cartridge with a new (filled) cartridge.

Aside from replacing the empty cartridge with a new cartridge, the user must somehow prepare the dose setting mechanism for a new cartridge: the dose setting mechanism must be reset to a starting or initial position. For example, in certain typical resettable devices, in order to reset the dose setting mechanism, the spindle that advances in a distal direction during dose injection must somehow be retracted back into the dose setting mechanism. Certain known methods of retracting this spindle back into the dose setting mechanism to a restart or an initial position are known in the art. As just one example, known reset mechanisms require a user to turn back or push back (retract) the spindle or some other portion of the dose setting mechanism.

Resetting of known dose setting mechanisms have certain perceived disadvantages. One perceived disadvantage is that the pen device user has to disassemble the device to either remove an empty cartridge or somehow reset the device. As such, another perceived disadvantage is that such devices have a high number of parts and therefore such devices are typically complicated from a manufacturing and from an assembly standpoint. For example, certain typical resettable pen type devices are not intuitive as to how a user must replace an empty cartridge and reset the device. In addition, because such resettable devices use a large number of components parts, such resettable devices tend to be large and bulky, and therefore not easy to carry around or easy to conceal.

There is, therefore, a general need to take these disadvantages associated with resetting issues into consideration in the design and development of resettable drug delivery devices. Such desired drug delivery devices would tend to reduce the number of component parts and also tend to reduce manufacturing costs while also making the device less complex to assemble and manufacture. Such desired devices would also tend to simplify the steps required for a user to reset a dose setting mechanism while also making the device less complex and more compact in size.

SUMMARY

It is an object of the present invention to provide an improved resetting mechanism for a reusable drug delivery device.

This object is solved by a driver (e.g. drive sleeve) for driving a spindle of a drug delivery device comprising a first component part (or portion) and a second component part (or portion) rotationally coupled to said first component part. During resetting of the drug delivery device, the first component is rotationally decoupled from the second component. In other words a driver for driving a spindle of a drug delivery device, comprises a first component part; and a second component part operatively coupled to the first component part. During a dose setting of the drug delivery device, both the first and the second component part rotate together. In addition, during resetting of the drug delivery device, the first component is decoupled from the second component and is free to rotate while the second component is prevented from rotating. The first component part may be a unitary molded component.

According to an embodiment of the invention the driver further comprises a spindle, wherein during resetting of said drug delivery device, said spindle is reset to an initial position. Preferably, during said resetting of said drug delivery device, said spindle is reset to said initial position by moving said spindle in an axial direction. This movement may be an axial displacement or a combination of an axial displacement with a rotation, i.e. a movement on a helical path.

Decoupling of said first and second components of the driver may be achieved by moving said first component in an axial direction. According to an embodiment said first component is decoupled from said second component by moving said first component in an axial direction away from said second component. Alternatively, said first component may be decoupled from said second component by moving said first component in an axially direction towards said second component.

When the device is used to inject a set dose of medication, both said first component and said second component rotate and/or move in an axial direction. Preferably, the driver (including both said first component and said second component) does not rotate but rather moves in an axial direction towards a distal end of said drug delivery device to thereby drive said spindle in said axial direction when said drug delivery device is used to inject said set dose of medication.

In another arrangement, a resettable dose setting mechanism for use with a drug delivery device comprises an outer housing and a rotating sleeve in rotatable engagement with respect to the outer housing. A driver having a first component and a second component, said first and said second component being operatively coupled together. A spindle is operatively coupled to the drive sleeve. When a user sets a dose by rotating the rotating sleeve, both the first and second component of the driver rotate together. When the user resets the dose setting mechanism, the first component is decoupled from the second component and the first component can rotate back to a starting position.

The dose setting mechanism may further comprise a cartridge holder releasably coupled to said dose setting mechanism, e.g. by way of a bayonet coupling. The cartridge holder may comprise a removable cartridge e.g. containing a medicament.

Irrespective of the above features, the present invention relates to a drive mechanism suitable for an injection device, comprising a housing and a pusher being movable relative to the housing with the pusher being coupled to the housing via first and second coupling means. The first coupling means comprise first engagement means of the housing and the pusher, respectively, cooperating with each other. Further, the second coupling means comprise a drive member, which is coupled to the pusher, and a dosing element, which is coupled to the drive member, with the dosing element being coupled to the housing via second engagement means. In addition, the drive mechanism provides for a third coupling means comprising a limiting element being coupled to the housing and having third engagement means for coupling the limiting element to the drive member. According to the invention the second coupling means is arranged to be decoupled at a position between the second engagement means and the third second engagement means.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates an example of a resettable drug delivery device;

FIG. 2 illustrates a further view of the first embodiment of the drug delivery device illustrated in FIG. 1;

FIG. 11 illustrates a second arrangement of the driver illustrated in FIGS. 6-8 comprising a first driver portion and a second driver portion.

DETAILED DESCRIPTION

Figure 3:
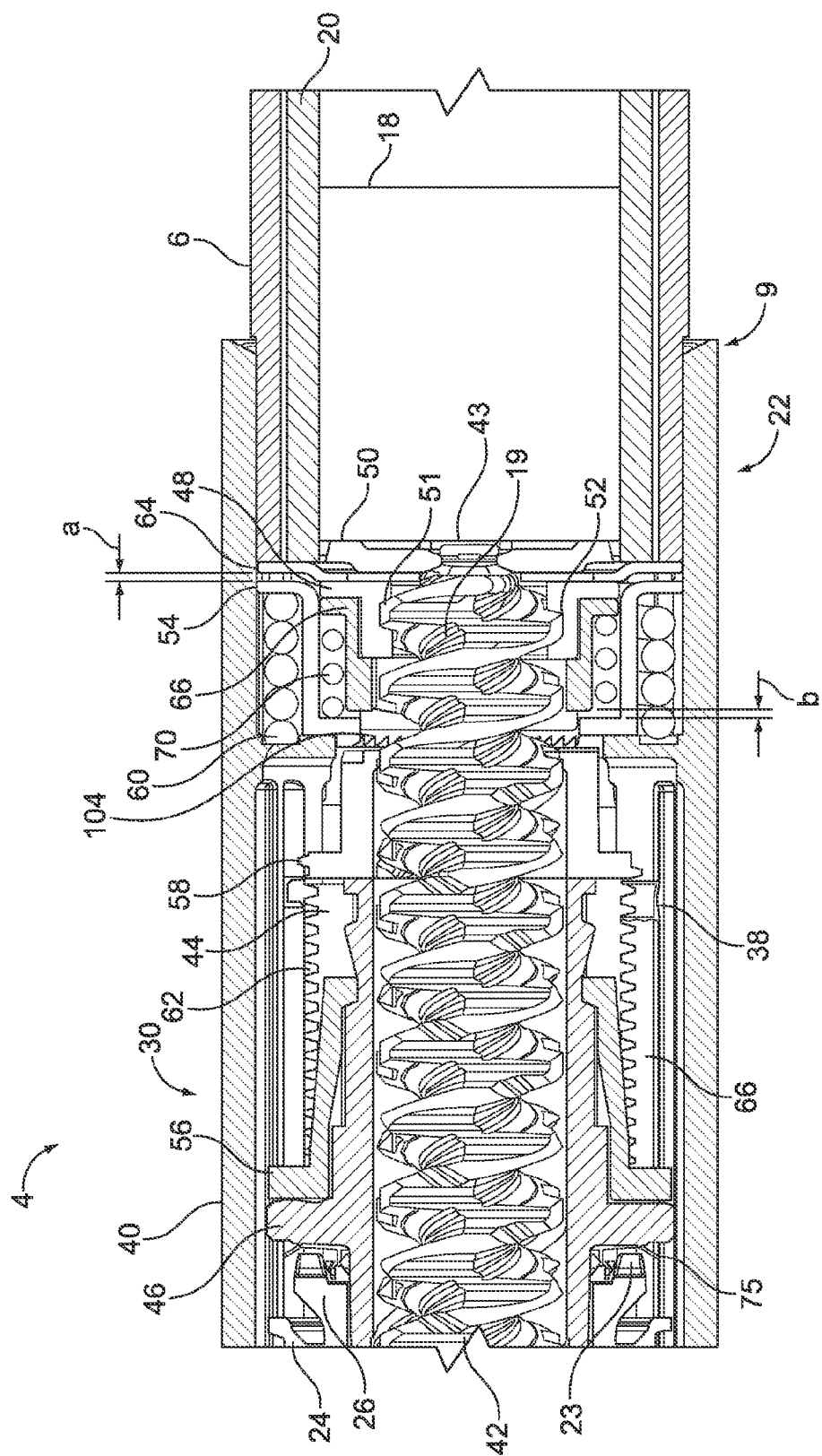
FIG. 3 illustrates a sectional view of the first embodiment of the drug delivery device of FIG. 2 in a first position.

The terms "drug" or "medicinal product" or "medicament", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Referring to FIG. 1, there is shown a drug delivery device 1 in accordance with a first arrangement of the present invention. The drug delivery device 1 comprises a housing having a first cartridge retaining part 2, and dose setting mechanism 4. A first end of the cartridge retaining means 2 and a second end of the dose setting mechanism 4 are secured together by retaining features. In this illustrated arrangement, the cartridge retaining means 2 is secured within the second end of the dose setting mechanism 4. A removable cap 3 is releasably retained over a second end or distal end of a cartridge retaining part. As will be described in greater detail, the dose setting mechanism 4 comprises a dose dial grip 12 and a window or lens 14. To set a dose of medication contained within the drug delivery device 1, a user rotates the dose dial grip 12 and the window allows a user to view the dialed dose by way of a dose scale arrangement 16.

FIG. 2 illustrates the medical delivery device 1 of FIG. 1 with the cover 3 removed from the distal end of the medical delivery device. As illustrated, a cartridge 20 from which a number of doses of a medicinal product may be dispensed is provided in the cartridge housing 6. Preferably, the cartridge 20 contains a type of medicament that must be administered often, such as once or more times a day. One such medicament is insulin. A bung or stopper (not illustrated in FIG. 2, cf. cartridge piston 18 in FIG. 3) is retained in a first end or a proximal end of the cartridge 20.

The dose setting mechanism 4 of the drug delivery device illustrated in FIG. 2 may be utilized as a reusable (and hence resettable) drug delivery device. Where the drug delivery device 1 comprises a reusable drug delivery device, the cartridge is removable from the cartridge housing 6. The cartridge 20 may be removed from the device without destroying the device but merely by the user disconnecting the dose setting mechanism 4 from the cartridge holder 6.

In use, once the removable cap 3 is removed, a user can attach a suitable needle assembly to the distal end of the cartridge holder. Such needle unit may be screwed onto a distal end of the housing or alternatively may be snapped onto this distal end. A replaceable cap 3 is used to cover the cartridge holder 6 extending from the dose setting mechanism 4. Preferably, the outer dimensions of the replaceable cap 3 are similar or identical to the outer dimensions of the dose setting mechanism 4 so as to provide an impression of a unitary whole when the replaceable cap 3 is in position covering the cartridge holder 2.

Figure 4:
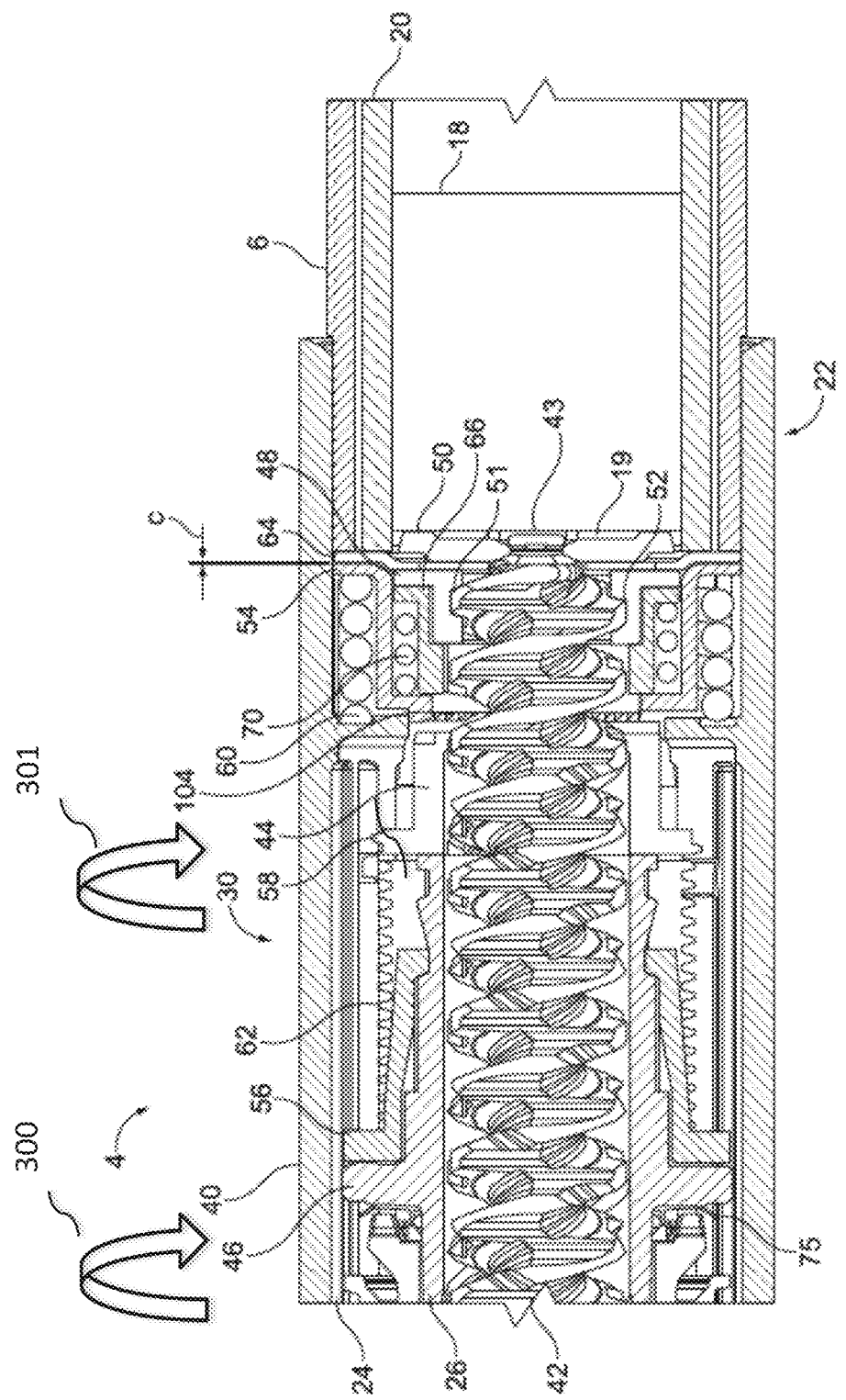
FIG. 4 illustrates a sectional view of the first embodiment of the drug delivery device of FIG. 2 in a second position.
Figure 5:
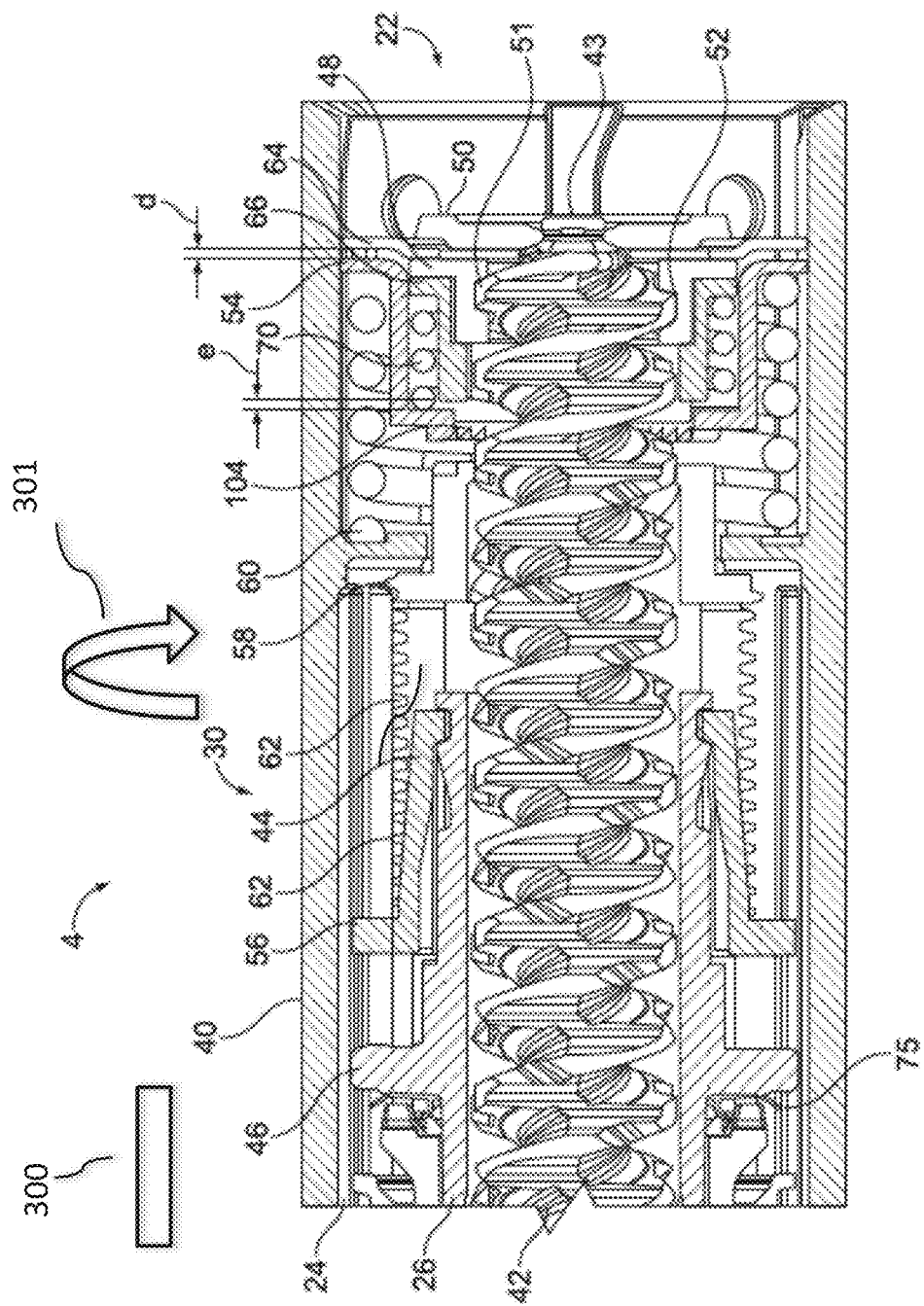
FIG. 5 illustrates a sectional view of the first embodiment of the drug delivery device of FIG. 2 in a third position.

FIGS. 3-5 show an example of a dose setting mechanism similar to that of the present invention. However, various aspects of this example, especially the general design and function of the driver, may be used in the present invention as will become apparent to those of ordinary skill in the art.

FIG. 3 illustrates a sectional view of the dose setting mechanism 4 removably connected to the cartridge holder 6. The dose setting mechanism 4 comprises an outer housing 40 containing a spindle 42, a number sleeve 24, a clutch 26, and a driver 30. A first helical groove 19 extends from a first end of a spindle 42. In one arrangement, the spindle 42 is generally circular in cross section however other arrangements may also be used. The first end of the spindle 42 (a distal end 43 of the spindle 42) extends through a pressure plate 64. A spindle bearing 50 is located at the distal end 43 of the spindle 42. The spindle bearing 50 is disposed to abut a second end of the cartridge piston 18. The driver 30 extends about the spindle 42.

The clutch 26 is disposed about the driver 30, between the driver 30 and a number sleeve 24. The clutch 26 is located adjacent the second end of the driver 30. A number sleeve 24 is provided outside of the clutch 26 and radially inward of the housing 40. The main housing 40 is provided with a window 14 through which a part of an outer surface of the number sleeve 10 may be viewed.

Returning to FIGS. 1-2, a dose dial grip 12 is disposed about an outer surface of the second end of the number sleeve 10. An outer diameter of the dose dial grip 12 preferably corresponds to the outer diameter of the housing 40. The dose dial grip 12 is secured to the number sleeve 10 to prevent relative movement between these two components. In one preferred arrangement, the dose dial grip 12 and number sleeve 10 comprise a one piece component that is rotationally coupled to a clutch and drive sleeve and axially coupled to the number sleeve 10. However, alternative coupling arrangements may also be used.

Returning to FIGS. 3-5, in this arrangement, driver 30 comprises a first driver portion 44 and a second driver portion 46 and these portions extend about the spindle 42. Both the first and the second driver portions 44, 46 are generally cylindrical. As can be seen from FIG. 6, the first drive portion 44 is provided at a first end with a first radially extending flange 56. A second radially extending flange 58 is provided spaced a distance along the first driver portion 44 from the first flange 56. An intermediate helical groove 62 is provided on an outer part of the first driver portion 44 extending between the first flange 56 and the second flange 58. A portion or a part helical groove 68 extends along an internal surface of the first driver portion 44. The spindle 42 is adapted to work within this part helical groove 68.

A dose limiter 38 (illustrated in FIG. 3) is located between the driver 30 and the housing 4, disposed between the first flange 56 and the second flange 58. In the illustrated arrangement, the dose limiter 38 comprises a nut. The dose limiter 38 has an internal helical groove matching the helical groove 62 of the driver 30. In one preferred arrangement, the outer surface of the dose limiter 38 and an internal surface of the housing 40 are keyed together by way of splines. This prevents relative rotation between the dose limiter 38 and the housing 40 while allowing relative longitudinal movement between these two components.

Referring back to FIGS. 2-5, essentially, in normal use, the operation of the dose setting mechanism 4 occurs as follows. To dial a dose in the arrangement illustrated in FIGS. 1-5, a user rotates the dose dial grip 12. The driver 30, the clutch 26 and the number sleeve 10 rotate along with the dose dial grip 12.

The number sleeve 10 extends in a proximal direction away from the housing 40. In this manner, the driver 30 climbs the spindle 42. At the limit of travel, a radial stop on the number sleeve 10 engages either a first stop or a second stop provided on the housing 40 to prevent further movement. Rotation of the spindle 42 is prevented due to the opposing directions of the overhauled and driven threads on the spindle 42. The dose limiter 38, keyed to the housing 40, is advanced along the thread 66 by the rotation of the driver 30.

FIG. 2 illustrates the medical delivery device after a desired dose of 79 International Units (IU) has been dialed. When this desired dose has been dialed, the user may then dispense the desired dose of 79 IU by depressing the dial grip 12. As the user depresses the dial grip 12, this displaces the clutch 26 axially with respect to the number sleeve 10, causing the clutch 26 to disengage. However the clutch 26 remains keyed in rotation to the driver 30. The number sleeve 10 is now free to rotate.

The driver 30 is prevented from rotating with respect to the main housing 40 but it is free to move axially with respect thereto. The longitudinal axial movement of the driver 30 causes the spindle 42 to rotate and thereby to advance the piston 18 in the cartridge 20.

In normal use, the first and second portions 44, 46 of the driver 30 are coupled together when the dose dial sleeve 10 is rotated. That is, in normal use, the first and second portions 44, 46 of the driver 30 are coupled together with the dose dial sleeve 10 when a user sets a dose by turning the dose dial grip 12. After each dispensed dose, the spindle 42 is pushed in a distal direction, acting on the bung 18 of the cartridge 20 to continue to expel a dialed dose of medication out of an attached needle assembly releasably connected to the distal end 8 of the cartridge holder 6.

After a user uses the drug delivery device 1 to dispense all of the medication contained in the cartridge 20, the user may wish to replace the empty cartridge in the cartridge holder 6 with a new cartridge. The user must then also reset the dose setting mechanism 4: for example, the user must then retract or push the spindle 42 back into the dose setting mechanism 4.

If the user decides to replace an empty cartridge and reset the device 1, the first and second driver portions 44, 46 must be de-coupled from one another. After decoupling the first driver portion 44 from the second driver portion 46, the first driver portion 44 will be free to rotate while the second driver portion 46 will not be free to rotate.

Figure 7:
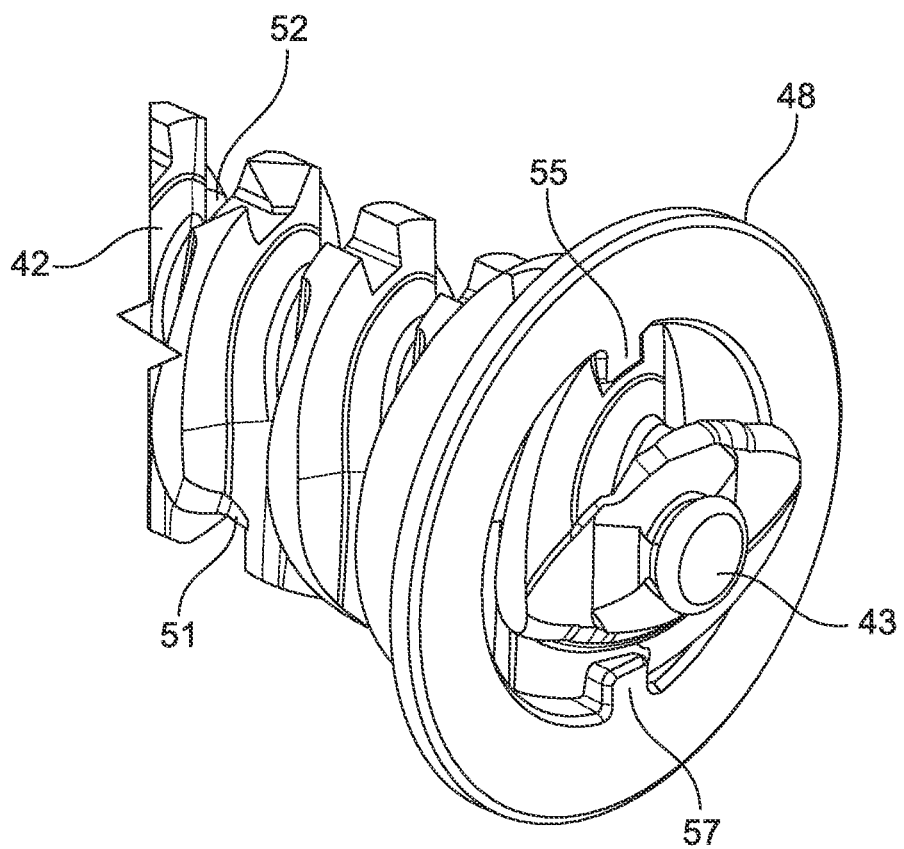
FIG. 7 illustrates a distal end of the spindle of the dose setting mechanism illustrated in FIGS. 2-5.

During a device resetting step, rotating the first driver portion 44 achieves at least two results. First, rotation of the first driver portion 44 will reset the axial position of the spindle 42 with respect to the dose setting mechanism 4 since rotation of the first driver portion 44 causes the spindle 42 to rotate. Rotation of the spindle 42 (because the spindle is splined with the spindle guide 48) move in a proximal direction back into the dose setting mechanism. For example, FIG. 7 illustrates one arrangement for connecting the spindle 42 to the spindle guide 48. In FIG. 7, the spindle 42 comprises a first spline 51 and a second spline 52. The spindle guide 48 comprises an essentially circular member having an aperture. The aperture includes two inner protruding members 55, 57 that engage the first and second splines 51, 52 respectively, so that the spindle guide 48 locks onto the spindle and rotates along with the spindle during spindle rotation.

Second, rotation of the first driver portion 44 will also axial move or reset a dose limiter 38 to an initial or start position. That is, as the first driver portion 44 is rotated back to an initial start position, because the dose limiter 38 is threadedly engaged to the outer groove and splined to an inner surface of a housing portion, such as the outer housing 40. In this configuration, the dose limiter 38 is prevented from rotating but will move along the outer groove 62 of the first driver portion 44 as this portion is rotated during a resetting step.

Referring to a first driver arrangement illustrated in FIG. 3, the two portions of the driver 30 are decoupled when the first driver portion 44 is pulled axially away from the second driver portion 46. This may be achieved by the use of a biasing means (such as at least one spring) that interacts together when the cartridge holder 6 is removed from the front or distal end of the device to first lock the relative rotation between the spindle 42 and a spindle guide 48 through which the spindle passes, and then to push this spindle guide 48 and also nut 66 axially a fixed distance. Because the spindle 42 is rotationally locked to this spindle guide 48 and is threadedly engaged with the spindle nut 66, the spindle 42 will move axially.

The spindle 42 is coupled via a groove engaged to the first driver portion 44. The first driver portion 44 is prevented from rotation by a clutched connection to the second driver portion 46. In one preferred arrangement, the second driver portion 46 is prevented from rotation by a clicker detent 75. The clicker detent 75 resides between the clutch and the flange 80 on the drive sleeve 46. Therefore, axial movement of the spindle 42 decouples the two driver portions 44, 46 so that the clutched connection becomes de-coupled.

This sequence of operation as the cartridge holder 6 is removed or disconnected from the dose setting mechanism 4 is illustrated in FIGS. 3-5. In FIG. 3, the various component parts of the drug delivery device include: a dose setting housing 40, a cartridge 20, a spindle 42, first driver portion 44; second driver portion 46, spindle bearing 50, spindle guide 48, a spring plate 54; a main spring 60, a pressure plate 64, a cartridge holder 20; a spindle nut 66; and a second spring 70. In this preferred arrangement, the spindle guide 48 is rotationally fixed relative to the spindle 20. In addition, the spring plate 54, pressure plate 64 and spindle nut 66 are all rotationally fixed relative to the outer housing.

In FIG. 3, the cartridge holder 6 is fitted via apertures in the pressure plate 64 and applies a load to the spring plate 54. This compresses the first biasing means or main spring 60. These apertures in the pressure plate 64 (not shown) allow the pressure plate 64 to move away from the spring plate 54 (in a distal direction towards the cartridge holder 6) under the action of the second biasing means or second spring 70. This will open up a Gap "a" as shown in FIG. 3. Gap "a" is a gap created between the pressure plate 64 and the spring plate 54. This will also open Gap "b", a gap between the spindle nut 66 and the spring plate 54. This Gap b is illustrated in FIG. 3. The Gap b in conjunction with the light force from the second spring or biasing means 70 moves the spindle nut 66 towards the distal end of the drug delivery device 1. This applies light pressure to the spindle guide 48.

The spindle guide 48 is compressed under the action of the second spring 70 between the spindle nut 66 and pressure plate 64. This light force coupled with the friction coefficient on either side of a flange of the spindle guide 48 through which this force acts, provides a resistance to rotation of the spindle guide 48 and therefore a resistance to rotation of spindle 42 as well. One advantage of this configuration is that at the end of a dose, it is advantageous to prevent the spindle 42 from back-winding into the dose setting mechanism 4 under light residual loads that may remain from the cartridge bung 18. By preventing the spindle 42 from back-winding in a proximal direction, a distal end 43 of the spindle 42 (and hence the spindle bearing 50) remains on the bung 18. Maintaining the distal end 43 of the spindle 42 on the bung 18 helps to prevent a user from administrating a potential under-dose.

When the user delivers a dose, as the dispense force increases, the rearward load on the spindle nut 66 increases to a point at which the spindle nut 66 travels back in a proximal direction and compresses the second spring 70. This releases the axial force acting on the spindle guide 48. This removes the resistance to rotation of the spindle guide 48 and hence spindle 42. This configuration therefore prevents back-winding of the spindle 42 under low loads caused by the cartridge bung 18, but does not add to the dispense force once this dispense force has increased above a certain threshold level.

FIG. 4 illustrates the dose setting mechanism 4 of FIG. 3 with the cartridge holder 6 rotated to release a connection type between the housing 40 of dose setting mechanism 4 and the cartridge holder 6. In one arrangement, this connection type 22 is a bayonet connection. However, those of ordinary skill in the art will recognize that other connection types 22 may be used as well such as threads, snap locks, snap fits, luer locks and other similar connection types. In the arrangement illustrated in FIGS. 3-5, by rotating the cartridge holder 6 with respect to housing 40, features that were initially acting on the spring plate 54 to compress the main biasing means 60 through apertures in the pressure plate 64, rotate so that they now release this force created by the main biasing means 60. This allows the spring plate 54 to move in a distal direction until the spring plate 54 contacts the spindle nut 66 on an inside face of the spindle nut 66.

In this second condition, the previous discussed Gap "a" (from FIG. 3) has now been reduced to a Gap "c" (as seen in FIG. 4). In this manner, the relative high axial force from the main biasing means 60 acts through the spring plate 54 to the spindle nut 66 and from the spindle nut 66 through the spindle guide 48 to the pressure plate 64. This relative high axial force from the main biasing means 60 is sufficient to prevent the spindle guide 48, and hence spindle 42, from rotating.

After sufficient rotation of the cartridge holder 6, the cartridge holder 6 disengages from the connection type 22 with the housing 40. The cartridge holder 6 is then driven in an axial direction away from the housing 40 by the main biasing means 60 (i.e., in a distal direction). However, during this movement, the main spring 60 continues to load the cartridge holder 6 through the spindle guide 48 and therefore the spindle 42 is prevented from rotation. As the spindle 42 is also threaded to the first driver portion 44, the first driver portion 44 is also pulled axially in a distal direction and in this manner becomes disengaged from the second driver portion 46. The second driver portion 46 is axially fixed and is prevented from rotation. In one arrangement, the second driver portion 46 is prevented from rotation by clicker elements and prevented from axial movement by its axial coupling to the number sleeve.

FIG. 5 illustrates the dose setting mechanism illustrated in FIG. 3 in a third position, that is, with the cartridge holder 6 removed. As the cartridge holder 6 is removed from the housing 40, the bayonet features shown in FIG. 5 (illustrated as round pegs extending radially inwards on inside of inner housing), limit travel of the pressure plate 64 but allows Gap "c" (as shown in FIG. 4) to increase to a wider Gap "d" (as shown in FIG. 5). As a result, Gap "e" develops. Gap "e" removes the high spring force created by the main biasing means 60 from the spindle guide 48. The dose setting mechanism 4 in FIG. 4 is now ready to be reset.

To reset this dose setting mechanism 4, a user retracts the spindle 42 in a proximal direction back into the housing 40 by pushing on the distal end 43 of the spindle 42. Therefore, during this resetting step of the dose setting mechanism 4, as the spindle 42 is pushed back into the dose setting mechanism 4, the movement of the spindle 42 causes the spindle nut 66 to move back against a light spring force created by the second biasing means 70. This movement releases the axial load and hence resistance to rotation from the spindle guide 48. Therefore, as the dose setting mechanism 4 is reset by the spindle 42 rotating back into the dose setting mechanism 4, the spindle guide 48 also rotates.

As the spindle 42 is pushed back further into the dose setting mechanism 4, the spindle 42 rotates through the spindle nut 66. As the first driver portion 44 is de-coupled from the second driver portion 46, the first driver portion 44 rotates (with the flexible elements 102, 103 running on a conical surface groove 90 formed by the first annular ring 91 on the second half of the drive sleeve 46, FIGS. 5 and 6). This accommodates the axial and rotational movement of the spindle 42.

As the first driver portion 44 rotates during reset, first driver portion 44 also resets the dose nut. More specifically, as the first driver portion 44 rotates, the dose nut which is not rotatable since it is splined to an inner surface of the housing 40, traverses along the helical groove 62 provided along an outer surface of the first driver portion 44 and traverses back to an initial or starting position. In one preferred arrangement, this starting position of the dose nut resides along the first radial 56 flange of the first driver portion 44.

After the dose setting mechanism 4 has been reset, the dose setting mechanism 4 must be re-connected to the cartridge holder 6. When re-connecting these two components, the process generally works in reverse. However, this time the axial compression of the main spring 60 causes the first driver portion 44 to re-engage with the second driver portion 46. In this manner, the flexible elements re-engage with the second annular ring 94 on the second driver portion 46.

Figure 6:
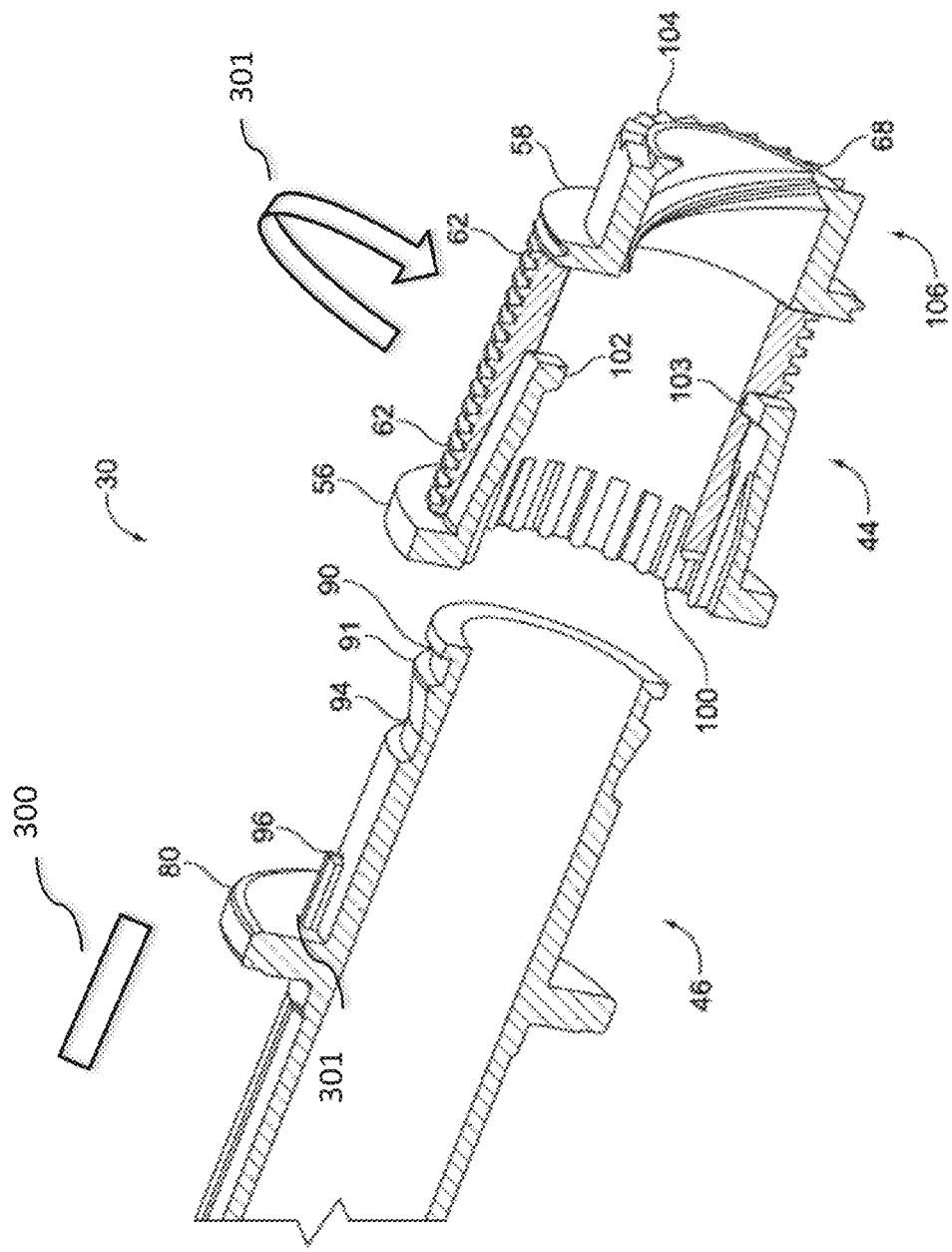
FIG. 6 illustrates a first arrangement of the driver illustrated in FIGS. 2-5 comprising a first driver portion and a second driver portion.

FIG. 6 illustrates a first arrangement of the second driver portion 46 and the first driver portion 44 illustrated in FIG. 3. As shown in FIG. 6, second driver portion 46 is generally tubular in shape and comprises a first annular groove 90 at a distal end of the second driver portion 46. The first annular groove 90 comprises a conical face 91. The second driver portion further comprises a second annular groove 94 and at least one spline 96 positioned along a surface of the second driver portion.

The first driver portion 44 is also generally tubular in shape and comprises a first and a second flexible element 102, 103 and a plurality of spline recesses 100. These plurality of recesses 100 releasably connect the longitudinal spline 96 of the first driver portion 44 to second driver portion 46 when both first and second driver portions 44, 46 are pushed axially together so that they releasably engage one another. When pushed together, the flexible elements 102, 103 of the first driver portion 44 are pushed over the first annular groove 90 of the second driver portion 46 and then stop when the flange 80 of the second driver portion abuts the first axial flange 56 of the first driver portion 44.

The first driver portion 44 also includes a plurality of ratchet features 104. These ratchet features 104 are provided at a distal end 106 of the first driver portion 44. These ratchet features 104 engage similar ratchet features on the spring plate 25 which are splined to the housing 2. (See e.g., FIGS. 3-5) At the end of the resetting step, these ratchet features engage one another so as to prevent the first driver portion 44 from rotating, thereby ensuring that as the spindle 42 is reset further, the first drive portion moves axially to re-engage the second drive portion 46 rather than rotate on the conical face 90. These features also orientate the spring plate 25 relative to the second driver portion 44 so that the two driver portions 44, 46 engage easily during assembly or after reset. Therefore, these ratchet features also prevent the coupling features 100, 96 from clashing with one another.

Figure 8:
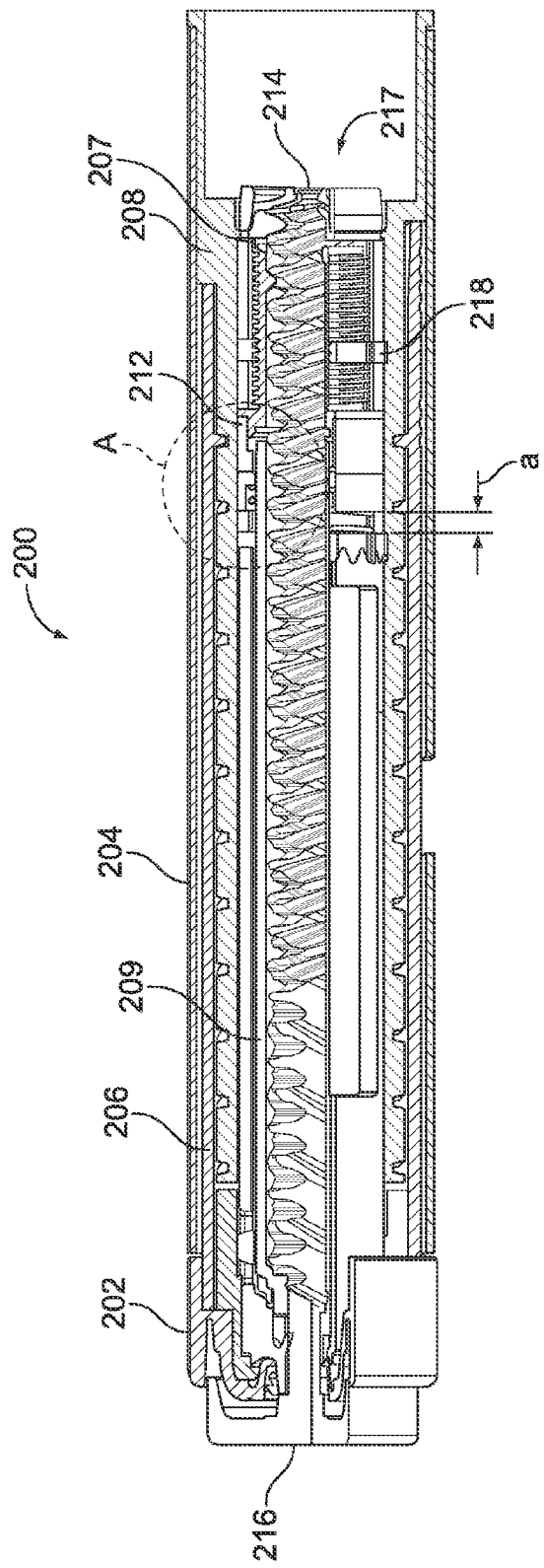
FIG. 8 illustrates a sectional view of a second embodiment of a dose setting mechanism of the drug delivery device illustrated in FIG. 1.
Figure 9:
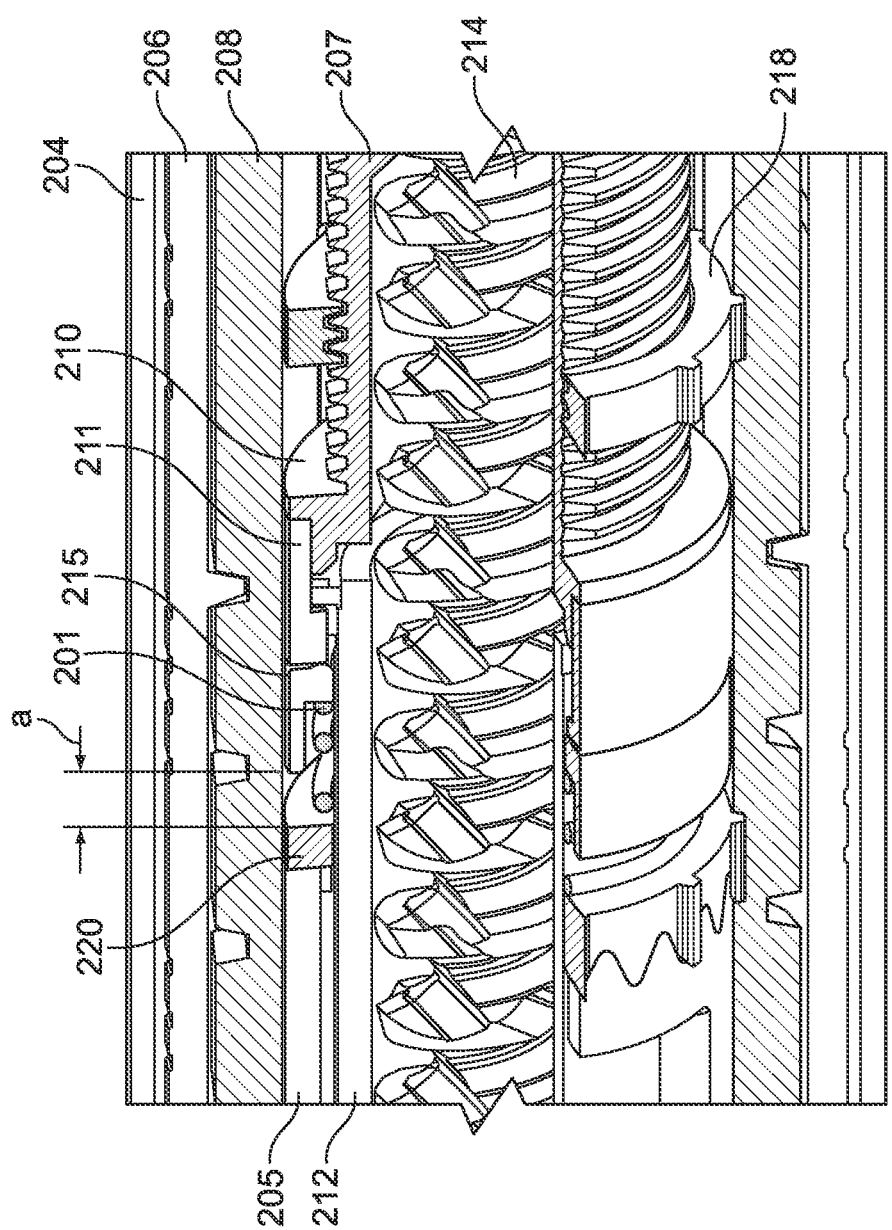
FIG. 9 illustrates a partial sectional view of the second embodiment of the dose setting mechanism illustrated in FIG. 8.
Figure 10:
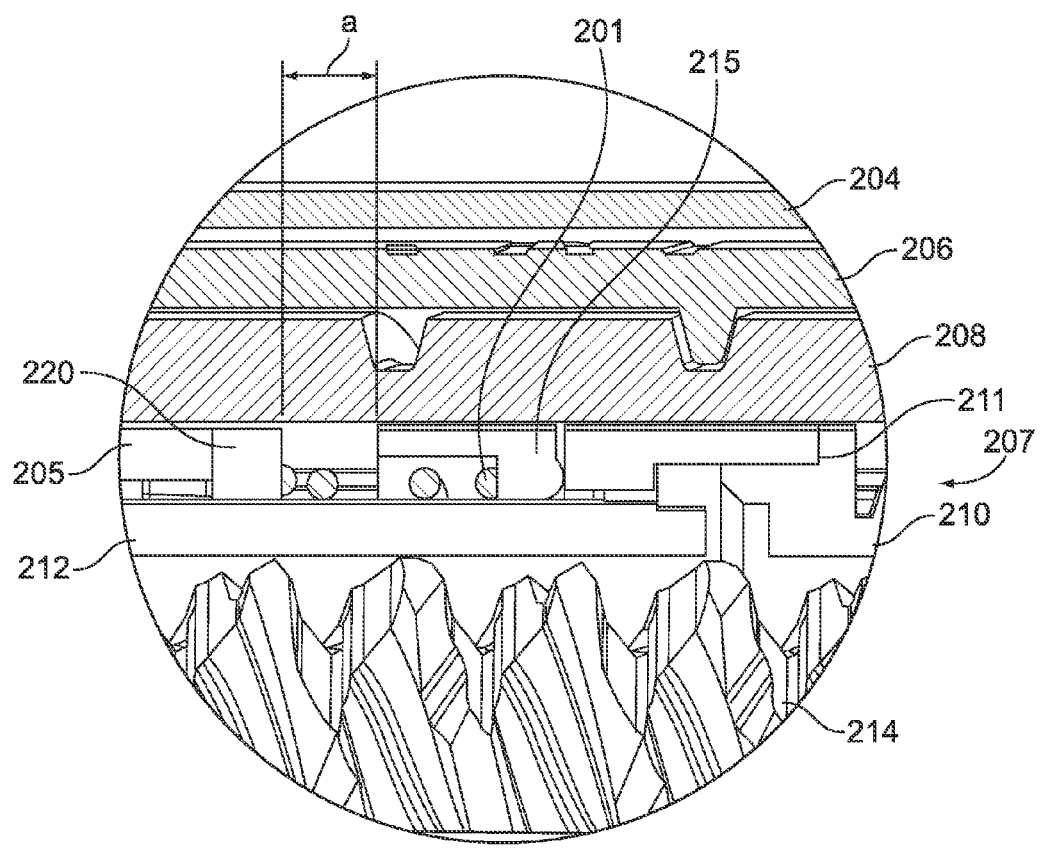
FIG. 10 illustrates a close up view of Gap a illustrated in FIG. 8.

A second arrangement of resettable dose setting mechanism is illustrated in FIGS. 8-10. FIG. 8 illustrates a section view of a second arrangement of a dose setting mechanism 200. Those of skill in the art will recognize that dose setting mechanism 200 may include a connection mechanism for releasably connecting to a cartridge holder, like the cartridge holder 6 illustrated in FIG. 2. FIG. 9 illustrates a portion of the dose setting mechanism illustrating the driver operation. FIG. 10 illustrates a close up view of the coupling between the first driver portion and the second driver portion illustrated in FIG. 9. The second arrangement of the dose setting mechanism 200 operates in a similar fashion to the first arrangement of the dose setting mechanism 4 illustrated in FIGS. 1-5.

With reference to FIGS. 8-10, the dose setting mechanism 200 comprises a dose dial grip 202, a spring 201, a housing 204, a clutch 205, a number sleeve 206, and an inner housing 208. Similar to the driver 30 illustrated in FIGS. 2-5, driver 209 of dose setting mechanism comprises a first driver portion 207 and a second driver portion 212. In one arrangement, the first driver portion 207 comprises a first component part 210 and a second component part 211. Alternatively, the first driver portion 207 is an integral component part.

As illustrated in FIGS. 8 and 9, the driver 209 is de-coupled from the dose setting mechanism 200 when the first driver portion 207 is pushed axially towards the second driver portion 212 (i.e., pushed in a proximal direction). In one arrangement, this may be achieved by pushing axially on a distal end of the spindle 214. This does not require any mechanism associated with removal of a cartridge holder. The mechanism is also designed such that the first and second driver portions 207, 212 and the spindle 214 remain locked together rotationally during dose setting as well as during dose administration.

FIGS. 4-6 illustrate the relative movement of the first driver portion 44 compared to the second driver portion 46 for two different states of the two-piece driver. FIG. 4 shows the first driver portion 44 coupled to and rotationally fixed to the second driver portion 46. The movement indicator 300 for the second driver portion 46 and the movement indicator 301 for the first driver portion 44 indicate this. In FIG. 4, where the two driver portions are coupled together the movement indicators 300 and 301, shown as arrows, indicate that both driver portions rotate together, for example, during dose setting. FIGS. 5 and 6, where the first and second driver portions are decoupled, for example, during the resetting of the device, the movement indicator 300 for the second driver portion 46 is a flat line indicating no movement, however, the movement indicator 301 for the first driver portion 44 is an arrow indicating that the first driver portion 44 can move relative to the stationary second driver portion 46.

An axial force on the spindle 214 causes the spindle 214 to rotate due to its threaded connection to the inner housing 208. This rotation and axial movement of the spindle 214 in turn causes the first driver portion 207 to move axially towards the second driver portion 212. This will eventually de-couple the coupling elements 250 between the first driver portion 207 and second driver portion 212. This can be seen from FIG. 11.

This axial movement of the first driver portion 207 towards the second driver portion 212 results in certain advantages. For example, one advantage is that the metal spring 201 will compress and will therefore close the Gap a illustrated in FIGS. 8-10. This in turn prevents the clutch 205 from disengaging from the clicker 220 or from the number sleeve 206. The second driver 212 is prevented from rotation since it is splined to the clutch 205. The clicker 220 is splined to the housing 204. Therefore, when the Gap a is reduced or closed up, the second driver portion 212 cannot rotate relative to either the housing 204 or the number sleeve 206. As a consequence, the number sleeve 206 cannot rotate relative to the housing 204. If the number sleeve 206 is prevented from rotating then, as the spindle 214 is refracted back into the dose setting mechanism 200 and thereby re-set, there will be no risk of the number sleeve 206 being pushed out of the proximal side of the dose setting mechanism 200 as a result of a force being applied on the spindle 214.

Similarly, when the drug delivery device is being dispensed, the user applies an axial load to a dose button 216. The dose button 216 is axially coupled to the clutch 205 and this prevents relative axial movement. Therefore, the clutch 205 moves axially towards the cartridge end or the distal end of the dose setting mechanism 200. This movement disengages the clutch 205 from the number sleeve 206, allowing for relative rotation while closing up the Gap a.

As described above, this prevents the clutch 205 from rotating relative to the clicker 220 and hence relative to the housing 204. However, in this scenario, it also prevents the coupling between the first driver portion 210 and the second driver portion 212 from becoming disengaged. Therefore, any axial load on the spindle 214 only disengages the first and second driver portions 207, 212 when the dose button 216 is not axially loaded. This therefore does not happen during dispense.

With the dose setting mechanism 200, as a user dials a dose with the dose dial grip 202, the metal spring 201 is selected to be strong enough to maintain engagement of both clutched couplings: the clutched coupling between the clutch 205 and the number sleeve 206 and clutched coupling between the first driver portion 207 and second driver portion 212.

FIG. 11 shows in detail of a first arrangement of the first driver portion 207 and the second driver portion 212 illustrated in FIG. 8. As illustrated in FIG. 11, the second driver portion 212 is generally tubular in shape and comprises at least one drive dog 250 located at a distal end of the second driver portion 212. The first driver portion 207 also has a generally tubular shape and comprises a plurality of recesses 252 sized to engage with the drive dog 250 on the second driver portion 212. The construction of the drive dog and recesses allow disengagement with the drive dog 250 when the first and second driver portions are axially pushed together. This construction also creates a rotational coupling when these components are sprung apart. A dose limiter 218 is provided on first driver portion 207 and operates similarly to the dose limiter 38 illustrated in FIG. 3.

In this arrangement, the first driver portion 207 comprises a first portion 211 that is permanently clipped to a second portion 210. In this arrangement, the first portion 211 comprises the drive dogs 252 and the second component 210 includes the outer groove for the last dose nut as well as an internal groove 254. This internal groove 254 is used to connect to the spindle 214 and drives the spindle 214 during dose administration.

In the illustrated arrangement, the internal groove 254 comprises a part helical groove rather than a complete helical groove. One advantage of this arrangement is that it is generally easier to manufacture.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A driver for driving a spindle of a drug delivery device in a distal direction to cause a distal end of the spindle to move from an initial position to act on a bung within a cartridge to a subsequent distal position, said driver comprising a first component and a second component rotationally coupled through a clutch to said first component,
    wherein during a dose setting operation the clutch is engaged so that the first and second components are coupled together to rotate together in unison relative to an outer housing and the spindle when a user dials a dose of medicament for administration causing the driver to move axially in a proximal direction and preventing the spindle from moving rotationally;
    wherein during resetting of said drug delivery device, said clutch is disengaged such that the first component is decoupled from said second component so that the first component can rotate relative to the second component causing the spindle to retract axially from the subsequent distal position in the proximal direction back to the initial position.

2. The driver of claim 1 wherein the first component comprises a first component part and a second component part.

3. The driver of claim 1 wherein the first component is an integral component part.

4. The driver of claim 1 wherein during resetting of said drug delivery device, said first component is decoupled from said second component by moving said first component in an axial direction.

5. The driver of claim 1 wherein when said drug deliver device is used to set a dose of medication, both said first component and said second component rotate together at a same rate.

6. The driver of claim 1 wherein when said device is used to inject a set dose of medication, both said first component and said second component rotate and/or move in an axial direction.

7. A resettable dose setting mechanism for use with a drug delivery device, said mechanism comprising
    a housing, a rotating sleeve in rotatable engagement with respect to said housing, the driver of claim 1 having a first component and a second component, said first and said second component being operatively coupled together, and a spindle operatively coupled to said driver,
    such that when a user sets a dose by rotating said rotating sleeve, both said first component and said second component of said driver rotate together, and
    such that when said user resets said resettable dose setting mechanism, said first component of said driver is decoupled from said second component of said driver and said first component can rotate back to an original position.

8. The resettable dose setting mechanism of claim 7 further comprising a cartridge holder releasably coupled to said resettable dose setting mechanism, wherein decoupling of said first component from said second component is effected by decoupling said cartridge holder from said resettable dose setting mechanism.

9. The resettable dose setting mechanism of claim 7 wherein decoupling of said first component from said second component is effected by an axial movement of said spindle.

10. The resettable dose setting mechanism of claim 7 further comprising a biasing means wherein decoupling of said first component from said second component is effected by said biasing means.

11. The resettable dose setting mechanism of claim 7 wherein said housing comprises an outer housing.

12. The resettable dose setting mechanism of claim 7 wherein said housing comprises an inner housing.

13. A dose setting mechanism for a drug delivery device comprising the driver of claim 1 and further comprising a spindle and a spindle guide engaged with said spindle, wherein during resetting of said drug delivery device, said spindle rotates while said spindle guide does not rotate.

14. A dose setting mechanism for a drug delivery device comprising the driver of claim 1 and further comprising a dose limiter wherein during resetting of said drug delivery device, said dose limiter is reset to an initial position.

15. A dose setting mechanism for a drug delivery device comprising the driver of claim 1 and further comprising a spindle wherein when said drug delivery device is used to inject a set dose of medication, said spindle translates.

* * * * *